United States Patent

Dosta (10) Patent No.: US 10,111,988 B2
(45) Date of Patent: Oct. 30, 2018

(54) POROUS THREE-DIMENSIONAL STRUCTURE OF POLYTETRAFLUOROETHYLENE (VERSIONS), DENTAL IMPLANT, VASCULAR IMPLANT AND TISSUE IMPLANT FOR SUBSTITUTION PLASTY OF SOFT TISSUES

(71) Applicant: Anatoli D. Dosta, Minsk (BY)

(72) Inventor: Anatoli D. Dosta, Minsk (BY)

(*) Notice: Subject to any disclaimer, the term of this patent is extended or adjusted under 35 U.S.C. 154(b) by 987 days.

(21) Appl. No.: 14/194,048

(22) Filed: Feb. 28, 2014

(65) Prior Publication Data

US 2014/0335472 A1    Nov. 13, 2014

Related U.S. Application Data

(63) Continuation of application No. PCT/BY2012/000001, filed on Apr. 4, 2012.

(30) Foreign Application Priority Data

Sep. 1, 2011   (BY) .................................. a20111162

(51) Int. Cl.
*A61C 8/00* (2006.01)
*A61L 31/14* (2006.01)
(Continued)

(52) U.S. Cl.
CPC .......... *A61L 31/146* (2013.01); *A61C 8/0012* (2013.01); *A61L 27/16* (2013.01);
(Continued)

(58) Field of Classification Search
CPC ... A61C 8/0016; A61C 8/0037; A61C 8/0012; A61C 8/0019; A61C 8/0036;
(Continued)

(56) References Cited

U.S. PATENT DOCUMENTS

| 7,691,141 | B2  | 4/2010 | Lewis et al. |
| 2003/0093157 | A1* | 5/2003 | Casares ................... A61L 27/48  623/23.73 |

(Continued)

FOREIGN PATENT DOCUMENTS

| BY | 11482 C1 | 12/2008 |
| GB | 2263908 A | 8/1993 |

(Continued)

OTHER PUBLICATIONS

International Search Report from International Application No. PCT/BY2012/000001 filed Apr. 4, 2012, dated Jul. 25, 2012.

(Continued)

*Primary Examiner* — Nicholas Lucchesi
(74) *Attorney, Agent, or Firm* — Patentbar International, P.C.

(57) ABSTRACT

A porous three-dimensional structure of polytetrafluoroethylene was created featuring an enhanced ability of soft tissue ingrowth, or, in the second embodiment, combining the properties of an enhanced ability of soft tissue ingrowth with a barrier for the deposition of the living tissue cells. In the first embodiment of the porous three-dimensional structure of polytetrafluoroethylene it contains the open through pores and the blind pores, uniformly distributed over the inner surfaces of the open pores and connected therewith, and is made of mixture of the free-flow polytetrafluoroethylene having the granules sized from 100 to 300 microns, and the constraint-flow polytetrafluoroethylene having the granules sized up to 20 microns. In the second embodiment of the porous three-dimensional structure at least one surface of the three-dimensional body is provided with a barrier layer.

20 Claims, 4 Drawing Sheets

(51) Int. Cl.
*A61L 27/16* (2006.01)
*A61L 27/56* (2006.01)
*C08L 27/18* (2006.01)
*C08J 9/24* (2006.01)
*C08J 9/34* (2006.01)
*A61L 31/04* (2006.01)

(52) U.S. Cl.
CPC ............. *A61L 27/56* (2013.01); *A61L 31/048* (2013.01); *C08J 9/24* (2013.01); *C08J 9/34* (2013.01); *C08L 27/18* (2013.01); *C08J 2205/05* (2013.01); *C08J 2207/10* (2013.01); *C08J 2327/18* (2013.01); *Y10T 428/1376* (2015.01); *Y10T 428/249921* (2015.04); *Y10T 428/249976* (2015.04)

(58) Field of Classification Search
CPC ................ A61C 8/0022; A61C 8/0075; A61C 2008/0046; A61B 6/02; A61B 6/14; A61L 31/146; A61L 27/16; A61L 27/56; A61L 31/048; C08J 9/34; C08J 27/18; C08J 2205/05; C08J 2207/10; C08J 2327/18; Y10T 428/1376; Y10T 428/249921; Y10T 428/249976
See application file for complete search history.

(56) References Cited

U.S. PATENT DOCUMENTS

| | | |
|---|---|---|
| 2005/0112397 A1 | 5/2005 | Rolfe et al. |
| 2006/0129227 A1* | 6/2006 | Hengelmolen ........... A61F 2/91 623/1.16 |
| 2009/0182425 A1* | 7/2009 | Duda ................... A61K 9/0024 623/11.11 |
| 2009/0208907 A1* | 8/2009 | Dosta ................... A61C 8/0009 433/174 |
| 2012/0184960 A1* | 7/2012 | Dosta ................. A61B 17/8028 606/71 |
| 2015/0082757 A1* | 3/2015 | Chaen .................. B32B 27/322 55/482 |
| 2016/0242821 A1* | 8/2016 | Deneuvillers ...... A61B 17/7062 |

FOREIGN PATENT DOCUMENTS

| | | |
|---|---|---|
| RU | 2270640 C1 | 2/2006 |
| WO | 19970024084 A1 | 7/1997 |
| WO | 19970036954 A1 | 10/1997 |
| WO | 20050107829 A2 | 11/2005 |
| WO | 20080052300 A1 | 5/2008 |
| WO | 20100139041 A1 | 12/2010 |
| WO | 20110006228 A1 | 1/2011 |

OTHER PUBLICATIONS

A. Medvedev, Comparative evaluation of polypropylene and polytetrafluoroethylene implants during the planned removal of groin hernia. Abstract of thesis 2009.

Vityaz P. A. et al., Porous powder materials and the products thereof, Minsk "Vysheyshaya shkola" 1987, p. 115.

* cited by examiner

POROUS THREE-DIMENSIONAL STRUCTURE OF POLYTETRAFLUOROETHYLENE (VERSIONS), DENTAL IMPLANT, VASCULAR IMPLANT AND TISSUE IMPLANT FOR SUBSTITUTION PLASTY OF SOFT TISSUES

RELATED APPLICATIONS

This Application is a Continuation application of International Application PCT/BY2012/000001, filed on Apr. 4, 2012, which in turn claims priority to Belorussian Patent Applications No. BY a 2011 1162, filed Sep. 1, 2011, both of which are incorporated herein by reference in their entirety.

FIELD OF THE INVENTION

The invention being claimed relates to medical devices, in particular to the devices that can be used in the manufacture of implants for endoprosthesis replacement of soft or vascular tissues, replacement of the corresponding tissue in cardiology, vascular surgery, traumatology and orthopedics, dentistry.

BACKGROUND OF THE INVENTION

The polymeric porous three-dimensional structures are known [1, 2].

The porous three-dimensional structure of polytetrafluoroethylene [3] is known, made as a three-dimensional body and chosen as a nearest prior art reference for both the first and the second versions of the claimed structure.

The deficiencies of the known porous three-dimensional structure are the insufficient ingrowth ability of soft tissues, the absence of a barrier for deposition thereon and penetration of living tissue cells, in particular microorganisms, therein.

The a nearest prior art reference to the claimed dental implant is the implant, described in [4], comprising an abutment for formation of a dental prosthesis and a surface being in contact with the osseous tissue, having a biologically compatible metal porous zone for the osseous tissue ingrowth and a head for the gingival soft tissue ingrowth in the form of a porous three-dimensional structure of polytetrafluoroethylene positioned between the abutment of the dental prosthesis and the biologically compatible metal porous zone.

The deficiency of the known implant is the insufficient ingrowth ability of the gingival tissue as well as the insufficient protection against penetration of microorganisms into the area of osseo-to-porous metal area contact surface, which is the cause of a long-term engraftment of the implant and, in some cases, of rejection thereof.

The closest to the claimed vascular implant is the implant, described in [5]; it is made of GORATEKS-type porous polytetrafluoroethylene in the form of a tubular body of a given diameter.

However, as the company-applicant (and also the manufacturer of GORATEKS material) admits, the known vascular implants provoke deposition of the blood cells and formation of thrombi.

The a nearest prior art reference to the claimed implant is a tissue implant for the substitution plasty of soft tissues (anterior abdominal wall of the recipient) made of a monocomponent polytetrafluoroethylene film with a magnified diameter of micro-perforations up to 50-70 μm and with no middle nonporous layer, described in [6]; it has advantages over the bicomponent implants having the micro-perforations sized from 5 to 50 μm due to the optimized integration into the tissues.

The deficiency of the known tissue implant is the insufficient permeability for blood elements and soft tissue cells, resulting in a slow engraftment thereof.

SUMMARY OF THE INVENTION

The aim of the claimed invention is to create a porous three-dimensional structure of polytetrafluoroethylene featuring an enhanced ability of soft tissue ingrowth, or combining the properties of an enhanced ability of soft tissue ingrowth with a barrier for the deposition of the living tissue cells, as well as creation of an advanced dental implant, vascular implant and tissue implant for the substitution plasty of soft tissues.

The task set in the first embodiment of the porous three-dimensional structure of polytetrafluoroethylene in the form of a three-dimensional body, is solved owing to the fact that it contains the open through pores and the blind pores, uniformly distributed over the inner surfaces of the open pores and connected therewith, and is made of mixture of the free-flow polytetrafluoroethylene having the granules sized from 100 to 300 microns, and the constraint-flow polytetrafluoroethylene having the granules sized up to 20 microns.

Preferably the porous structure is made with the pores whose sizes are randomly distributed in the range of 150 to 300 microns.

It is preferred that the cumulative volume of the open pores is greater than the cumulative volume of the blind pores, and the average size of the blind pores may range from 0.01 to 1.0 of an average size of the open pores.

It is preferred that at least one surface of the three-dimensional body is provided with the barrier layer, which in a particularly preferred embodiment represents the layer of porous polytetrafluoroethylene, in which all of the pores are made blind.

The porous structure may be provided with a reinforcing element, preferably in the form of a braided or twisted three-dimensional structure of a titanium wire.

The task set in the second embodiment of the porous three-dimensional structure of polytetrafluoroethylene in the form of a three-dimensional body is solved owing to the fact that it contains the open through and the blind pores uniformly distributed over the inner surfaces of the open pores and connected therewith, and is made of mixture of the free-flow polytetrafluoroethylene having the granules sized from 100 to 300 microns, and the constraint-flow polytetrafluoroethylene having the granules sized up to 20 microns, provided that at least one surface of the three-dimensional body is provided with a barrier layer.

The barrier layer in a particularly preferred embodiment represents the layer of porous polytetrafluoroethylene, in which all of the pores are embodied closed.

Preferably the porous structure is made with the pores whose sizes are randomly distributed in the range of 150-300 microns.

The cumulative volume of the open pores is preferably greater than the cumulative volume of the blind pores, and the average size of the blind pores may range from 0.01 to 1.0 of the average size of the open pores.

The porous structure may be provided with the reinforcing element, preferably in the form of a braided or twisted three-dimensional structure of a titanium wire.

The presence of the additional blind pores uniformly distributed over the inner surfaces of the open pores in such a way that they connect with them, makes it possible to further increase the implant-to-tissue contact surface, stimulating the growth thereof and increasing the strength of adhesion as early as in the initial period. This is also promoted by making the open pores the through ones in all directions, eliminating the barrier for the blood flow through the structure in any direction and allowing to arrange it in the most natural way, which intensifies the nourishing of the growing tissue and reduces the likelihood of a recession.

The embodiment of the porous structure at the ratio of the cumulative volumes of the open and the blind pores more than 1, allows keeping low resistance of the structure to the blood flow in case of the additional increase of the tissue-to-porous structure contact surface.

The average size of the blind pores constitutes 0.01 to 1.0 of the medium size of open pores for ensuring the increased capillary pressure, firstly, promoting the improvement of the blood flow hydrodynamics and, as a consequence, the better nutrition of the growing tissue.

At the same time it should be noted that the claimed porous structure may have not enough strength for some of applications. For these use cases it can be provided with a reinforcing element, preferably in the form of braided or twisted three-dimensional structure of a titanium wire. Such a structure of the reinforcing element has no effect on the properties of the claimed porous structure (low resistance of the structure to the blood flow in case of the additional increase of the tissue-to-porous structure contact surface, increase of the adhesion strength as early as in the initial period, absence of barriers to blood flow through the structure), by means of increasing its strength and additionally providing an opportunity for the secure engagement of the suture material when suturing the tissue, for example, gingiva to the porous structure.

The task set in the dental implant, which includes an abutment for formation of a dental prosthesis, and a contacting with the osseous tissue surface, having a biologically compatible metal porous zone for the osseous tissue ingrowth and a head for the gingival soft tissue ingrowth in the form of a porous three-dimensional structure of the polytetrafluoroethylene positioned between the abutment of the dental prosthesis and the biologically compatible metal porous zone is solved owing to the fact that the head for the gingival soft tissue ingrowth is made of the claimed porous three-dimensional structure.

The height of the head for the ingrowth of the gingival soft tissue corresponds to the thickness of the gingival soft tissue. This is explained by the fact that complete ingrowth of epithelial cells into a porous three-dimensional structure of the head of polytetrafluoroethylene occurs, and a hermetic connection of the implant with the soft tissues is formed, creating the reliable barrier for the penetration of pathogenic microbes into the area of implantation from the oral cavity and contributing to the more secure fixation and strength of said implant seating in the jawbone.

The task set in the vascular implant, made of porous polytetrafluoroethylene in the form of a tubular body of a given diameter is solved owing to the fact that the specified material is a porous three-dimensional structure as claimed in the second embodiment, and the surface provided with the barrier layer is the inner surface of the tubular body.

The task set in the tissue implant for the soft tissue substitution plasty made of polytetrafluoroethylene, is solved owing to the fact that it is made of a porous three-dimensional structure as claimed in the first or the second embodiment.

BRIEF DESCRIPTION OF THE DRAWINGS

The essence of the claimed inventions is illustrated by the non-limiting drawings, where:

DETAILED DESCRIPTION OF THE PREFERRED EMBODIMENTS

Figure 1:
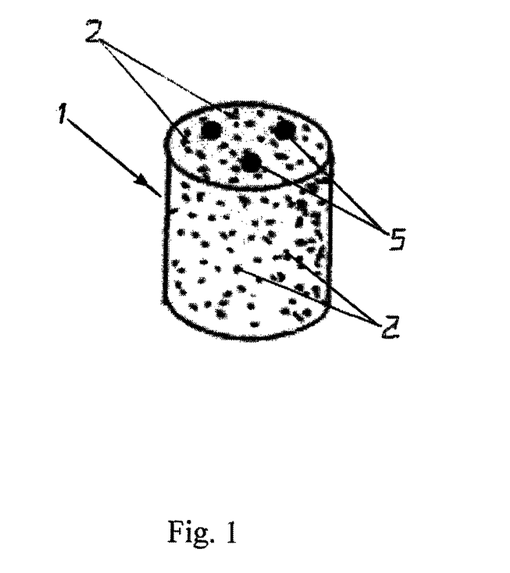
FIG. 1 and FIG. 2 illustrate the first and the second embodiments of the porous structure, respectively.
Figure 2:
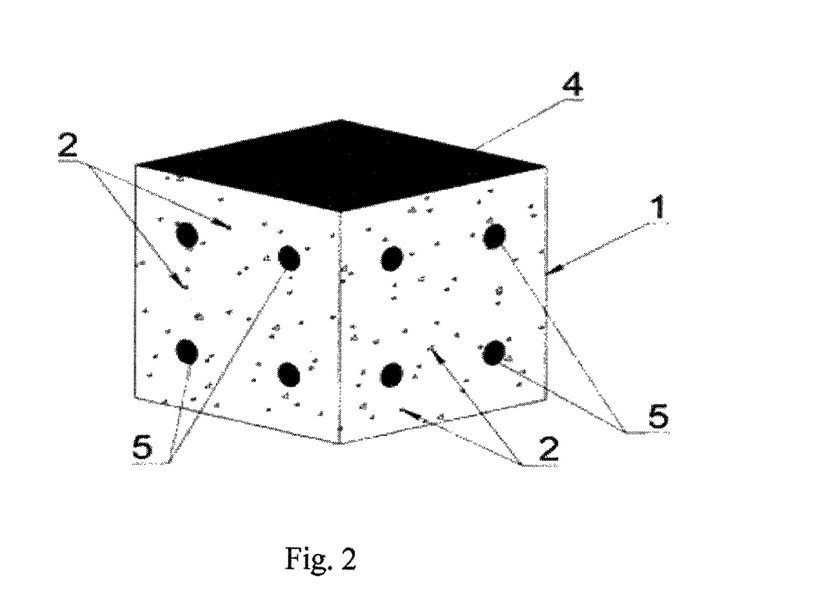
Figure 3:
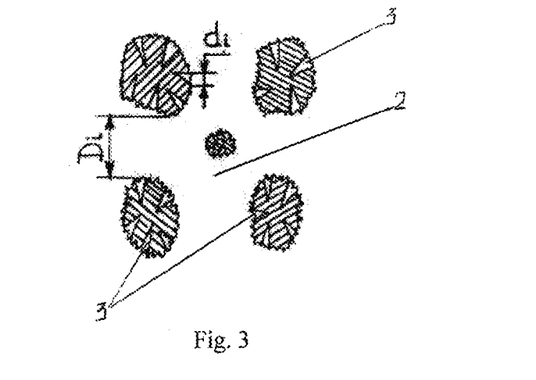
FIG. 3 is a cross-sectional view of the fragment of the claimed porous structure in scale of 1000:1, where $D_i$—average dimensions of open pores, $d_i$—average dimensions of dead-end pores.

The porous structure 1 is embodied of all sizes and shapes based on the requirements, for example, osteosynthesis (see FIGS. 1-2). Essential factors are three-dimensionality and commensurability (i.e., the size of the structure in three axes shall be of the same magnitude) as well as absence of an impermeable barrier in the form of a core or a substrate in the way of the bloodstream. All open pores 2 of the structure are through and equidirectional. Blind pores 3 (see FIG. 3) open additionally to the inner surfaces of the pores 2. The average dimension, $d_i$, of the blind pores 3 is 0.01-1.0 of the average dimension, $D_i$, of the open pores 2. The structure of this kind can be obtained by various techniques, for example, by foaming and thermofixation of the polymer solution. Another option to obtain the structure is pressing and sintering of the polymer powders. Formation of the dead-end pores 3 on the surfaces of the open pores 2 as well as the ratios of the dimensions and volumes thereof are achieved by adjusting the characteristics of the manufacturing process and by the ratio of the quantities of the free-flow polytetrafluoroethylene having the dimensions of the granules from 100 to 300 microns, and of the constraint-flow polytetrafluoroethylene having the dimensions of the granules up to 20 microns in the mixture, of which the claimed porous structure is made.

The second embodiment of the claimed porous structure is shown in FIG. 2 and differs by the presence of the barrier layer 4, in this example it is on the upper surface of the structure 1. The barrier layer 4 is a layer of porous polytetrafluoroethylene, in which all pores are closed. This kind of layer is formed, for example, in the process of manufacturing of the structure by the method of pressing and sintering of the polymer powders. It is formed both on the upper and on the lower surfaces of the structure, which can be divided horizontally into two products, each of them having a barrier layer. If necessary, the barrier layer may be removed from one or both surfaces of the structure.

As shown in the examples in FIGS. 1 and 2, the claimed porous structure is provided with the reinforcing element in the form of a three-dimensional structure 5, for example, knitted of a titanium wire.

Figure 4:
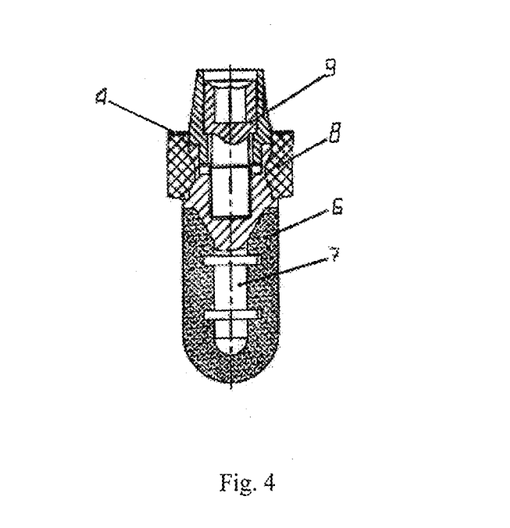
FIG. 4 illustrates schematically the general view of the dental implant with the claimed porous three-dimensional structure.

One of the forms of implementation of the claimed dental implant is shown in FIG. 4. The dental implant is made of a biocompatible material such as titanium, and has a shape of a cylindrical body having a proximal end and a distal end. Within a framework of this description the term 'proximal' means 'directed toward the hole in a jawbone during the implantation', and the term 'distal' means 'directed toward the oral cavity during the implantation'. The proposed dental implant contains a biologically compatible metal zone contacting the osseous tissue and representing a three-dimensional porous structure 6 of a cylindrical shape with a rounding at the proximal end in the form of a hemisphere. The three-dimensional porous structure 6 is manufactured of titanium powder, formed of a titanium sponge, pressed onto the frame 7, for example, using the method of hydrostatic pressing [7]. The dental implant has the head 8 for the ingrowth of the gingival soft tissue, made in the form of a collar positioned between the metal three-dimensional porous structure 6 and the abutment 9 for formation of a dental prosthesis. Head 8 is manufactured of the porous three-dimensional structure 1 of polytetrafluoroethylene, in this example, as claimed in the second embodiment. The structure is oriented so that the surface, being the barrier layer 4, is an upper surface of the head 8. After the placement of such an implant into the appropriate slot in the jaw, the gingival soft tissue is trimmed to the end of the head 8, and its upper surface, the barrier layer 4, does not allow microorganisms to penetrate inside of the head and further to the metal three-dimensional porous structure 6 and create a barrier for the ingrowth of the osseous tissue therein.

Embodiment of the porous structure with the reinforcing elements as claimed in the invention enables to additionally fasten the porous structure on the implant, to arrange the flow of blood through the pores in the anatomic direction, to increase the adhesive strength of the tissue with the porous structure. After the ingrowth of a spongy osseous tissue into the pores of the metal three-dimensional porous structure 6, and the ingrowth of the gingival tissue into the pores of the head 8 of the porous three-dimensional structure and the reliable fixation of the implant, the dental prosthesis is mounted onto the abutment 9 (for example, the screw or the threaded collar).

Figure 5:
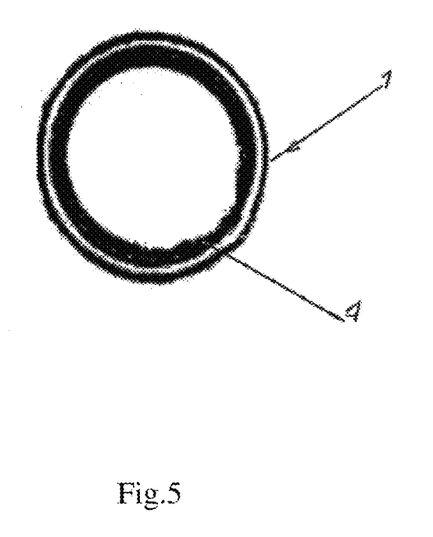
FIG. 5 illustrates schematically the cross section of the vascular implant, embodied in the form of a cylinder of the claimed porous three-dimensional structure as claimed in the second embodiment.

One of the forms of implementation of the vascular implant as claimed in the invention is shown in FIG. 5. The claimed implant is embodied in the form of a tubular body of a given diameter. The material of which the vascular implant is made is a porous three-dimensional structure as claimed in the second embodiment, at that, the surface provided with the barrier layer is the inner surface of the tubular body. The material of the porous structure features complete biocompatibility. When installing an implant by the known manner into the damaged vessel, the porous outer surface fits tightly against the inner surface of the vessel. As in the case described above, the claimed porous structure ensures implantation of the cells of the inner wall of the vessel into the porous structure. At the same time, the inner surface of the implant, the barrier layer 4, prevents the deposition of blood elements thereon, prevents formation of atherosclerosis plaques and thrombi.

The tissue implant for substitution plasty of soft-tissues as claimed in the present invention can be manufactured in the form of structure shown in FIG. 1 or FIG. 2. At that the porous structure is put into shape and size, roughly corresponding to the area subject to removal during the subsequent surgery, and determined based on the roentgenogram. Then, after the incision of the soft tissues, the damaged area is removed; the porous structure is implanted and secured. The wound is sewn up in layers.

Achievement of the claimed technical result was verified through the example of the dental implant in the process of clinical trials. The study was conducted in two mongrel dogs each weighing between 25 and 30 kg., at the age of 3 and 4 years. The dogs were healthy; their oral cavities had no signs of inflammation. The relevant permit for conductance of the surgeries was obtained from the Ethics Committee.

Under the general anesthesia after the treatment of the surgical field, after the dissection of the gingival soft tissues the implantation sites in the area of the upper and the lower jaw were uncovered. Seven dental implants were implanted into the implant beds. The heads made in the form of a ring of the porous structure as claimed in the present invention, encircling the neck of the implant, were fixed to the gingival tissue by the separate sutures.

Figure 6:
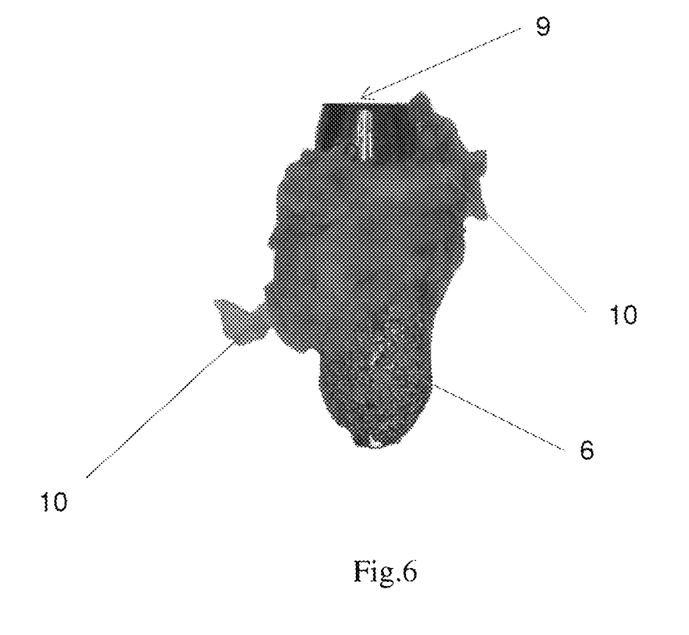
FIG. 6 illustrates the dental implant after its removal out of the jaw of an experimental animal in the course of clinical investigations, magnification: ×6.3.

In 50 days after the beginning of the experiment three implants were extracted in the operating-room conditions under general anesthesia. Three dental implants were subjected to macroscopic and microscopic examination. During the removal thereof, a fragment of soft tissue, fixed firmly in the area of the polytetrafluoroethylene ring, encircling the neck of the implant, was removed together with the implant. The volume of the tissues fused with the ring, varied a wide range. In one of the samples studied the contours of the ring were visible, in the other sample the thickness of the adjacent tissue 10 exceeded the thickness of the ring about twofold (FIG. 6). The remaining fragments of the implant were free of tissues.

The results of the interaction of the gingival tissues with the claimed porous structure are illustrated with the microphotographs of histological preparations shown in FIGS. 7A-7D, where the numbers denote: 1—polytetrafluoroethylene (does not perceive colorants), 2—fibrous connective tissue, 3—multilayered flat non-squamous epithelium. Micrographs were made with magnification A—×50; B—100, C, D—×400.

Figure 7A:
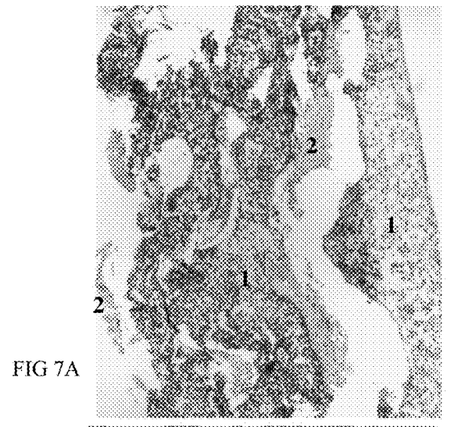
FIGS. 7A-7D show the photomicrographs of the histological specimens, illustrating the interaction of the gingival tissues with the porous polytetrafluoroethylene, magnification: A—×50, B—100, C, D—×400.
Figure 7B:
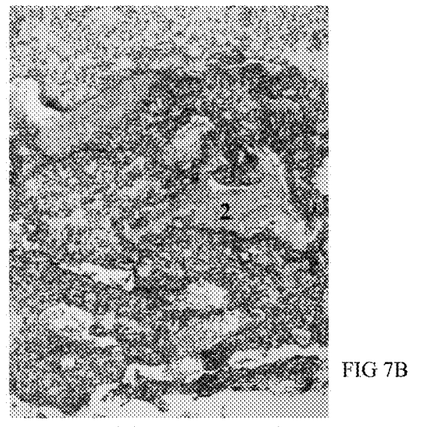
Figure 7C:
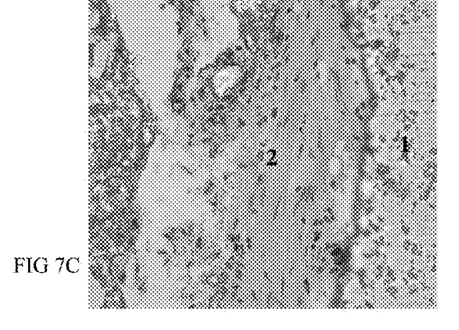
Figure 7D:
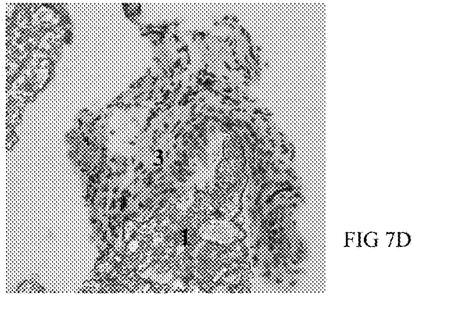

Histological examination established that the dense fibrous connective tissue interacts with ring around the neck of the tooth. It adjoins the surface of the ring and advances into the pores of the material of which the ring is made (FIG. 7A, 7B). The bundles of collagen fibers, as well as a large number of fibroblasts are clearly seen at the large magnification on the histological preparations stained with hematoxylin and eosin (FIG. 7C). The presence of the fragments of multilayered non-squamous epithelium interacting with the polytetrafluoroethylene insertion of the dental implant was revealed in the investigated samples (FIG. 7D).

Reactive inflammation is always evolving after the implantation in the gingival tissues. By the time of histological examination the signs of active inflammation process were preserved in one of the studied samples. In all appearances, the reason for this is the microorganisms penetrating from the oral cavity through the open-porous surface of the first embodiment of the claimed porous structure. Application of the second embodiment of the porous structure as claimed in the invention, eliminates penetration of microorganisms from the environment and, consequently, eliminates the inflammatory process emergence owing to the embodiment of the upper surface in the form of a barrier layer, in which all the pores are embodied closed.

The use of porous structure of the claimed design in cardiology, vascular surgery, traumatology and orthopedics, dentistry allows to increase the specific contact surface of the regenerated tissue and the implant, increase the characteristics of the ingrown tissue, accelerate the ingrowth of the tissue into the structure, as well as reduce the likelihood of a recession and the patient's rehabilitation time.

REFERENCES

1. WO 2005/107829, publ. 17. Nov. 2005
2. US 20050112397, publ. 26. May 2005
3. WO 97/24084, publ. 10.Jul. 1997
4. WO 2010/139041, publ. 09. Dec. 2010
5. U.S. Pat. No. 7,691,141, publ. 06 Apr. 2010
6. A. Medvedev Comparative evaluation of polypropylene and polytetrafluoroethylene implants during the planned removal of groin hernia. Abstract of thesis. 2009
7. Vityaz P. A. at al. Porous powder materials and the products thereof. Minsk, "Vysheyshaya Shkola" (Higher School), 1987, p. 115.

What is claimed is:

1. A material for implantation made of a mixture of free-flow polytetrafluoroethylene and constrained-flow polytetrafluoroethylene, the free-flow polytetrafluoroethylene comprising granules having a size from 100 to 300 microns, the constrained-flow polytetrafluoroethylene comprising granules having a size to 20 microns;
   the material for implantation having a porous three-dimensional structure formed as a three-dimensional body;
   the structure comprising open through pores and dead-ended pores uniformly distributed over inner surfaces of the open pores and connected with the inner surfaces;
   wherein a cumulative volume of the open pores is greater than a cumulative volume of the dead-ended pores, and wherein an average size of the dead-ended pores ranges from 0.01 to 1.0 of an average size of the open pores.

2. The material of claim 1, wherein sizes of the open through pores and the dead-ended pores are randomly distributed in the range from 150 to 300 μm.

3. The material of claim 1, wherein a portion of a surface of the three dimensional body is made in the form of a barrier layer, the barrier layer being a layer of porous polytetrafluoroethylene with all pores in the layer being closed.

4. The material of claim 1, wherein the structure further comprises a reinforcing element.

5. The material of claim 4, wherein the reinforcing element is made as a three dimensional structure which is braided or twisted of a titanium wire.

6. A material for implantation made of a mixture of free-flow polytetrafluoroethylene and constrained-flow polytetrafluoroethylene, the free-flow polytetrafluoroethylene comprising granules having a size from 100 to 300 microns, the constrained-flow polytetrafluoroethylene comprising granules having a size to 20 microns;
   the material for implantation having a porous three-dimensional structure formed as a three-dimensional body;
   the structure comprising open through pores and dead-ended pores uniformly distributed over inner surfaces of the open through pores and connected with the inner surfaces, wherein a cumulative volume of the open pores is greater than a cumulative volume of the dead-ended pores, and wherein an average size of the dead-ended pores ranges from 0.01 to 1.0 of an average size of the open through pores; and
   a portion of a surface of the three-dimensional body comprising a barrier layer, the barrier layer being a layer of porous polytetrafluoroethylene with all pores in the layer being closed.

7. The material of claim 6, wherein sizes of the open through pores and the dead-ended pores are randomly distributed in the range from 150 to 300 μm.

8. The material of claim 6, wherein the structure further comprises a reinforcing element.

9. The material of claim 8, wherein the reinforcing element is made as a three dimensional structure braided or twisted of a titanium wire.

10. A dental implant comprising:
    an abutment for forming a dental prosthesis, and a frame having a surface for being in contact with osseous tissue;
    the surface for being in contact with osseous tissue having a biologically compatible metal porous zone for the osseous tissue growing into the porous zone, and a head for a gingival soft tissue to grow into;
    the head being positioned between the abutment of the dental prosthesis and the biologically compatible metal porous zone; wherein the head is made of the material for implantation made of a mixture of free-flow polytetrafluoroethylene and constrained-flow polytetrafluoroethylene, the free-flow polytetrafluoroethylene comprising granules having a size of 100 to 300 microns, the constrained-flow polytetrafluoroethylene comprising granules having a size of 20 microns;
    the material for implantation having a porous three-dimensional structure formed as a three-dimensional body;
    the structure comprising open through pores and dead-ended pores uniformly distributed over inner surfaces of the open pores and connected with the inner surfaces;
    wherein a cumulative volume of the open pores is greater than a cumulative volume of the dead-ended pores, and wherein an average size of the dead-ended pores ranges from 0.01 to 1.0 of an average size of the open pores.

11. The dental implant of claim 10, wherein sizes of the open through pores and the dead-ended pores are randomly distributed in the range from 150 to 300 μm.

12. The dental implant according to claim 10, wherein a portion of a surface of the three dimensional body is made in the form of a barrier layer, the barrier layer being a layer of porous polytetrafluoroethylene with all pores in the layer being closed.

13. The dental implant according to claim 10, wherein the structure further comprises a reinforcing element.

14. A vascular implant in a form of a tubular body
    of a predetermined diameter made of the material for implantation made of a mixture of free-flow polytetrafluoroethylene and constrained-flow polytetrafluoroethylene, the free-flow polytetrafluoroethylene comprising granules having a size of 100 to 300 microns, the constrained-flow polytetrafluoroethylene comprising granules having a size to 20 microns;
    the material for implantation having a porous three-dimensional structure formed as a three-dimensional body;
    the structure comprising open through pores and dead-ended pores uniformly distributed over inner surfaces of the open through pores and connected with the inner surfaces, wherein a cumulative volume of the open pores is greater than a cumulative volume of the dead-ended pores, and wherein an average seize of the dead-ended pores ranges from 0.01 to 1.0 of an average size of the open through pores; and a portion of a surface of the three-dimensional body comprising a barrier layer, the barrier layer being a layer of porous polytetrafluoroethylene with all pores in the layer being closed, wherein a portion of the surface of the three-dimensional body comprising the barrier layer is an inner surface of the tubular body.

15. The vascular implant as in claim 14, wherein sizes of the open through pores and the dead-ended pores are randomly distributed in the range from 150 to 300 μm.

16. A tissue implant for a soft tissue plastic replacement made of the material for implantation made of a mixture of free-flow polytetrafluoroethylene and constrained-flow polytetrafluoroethylene, the free-flow polytetrafluoroethylene comprising granules having a size from 100 to 300 microns, the constrained-flow polytetrafluoroethylene comprising granules having a size to 20 microns;

the material for implantation having a porous three-dimensional structure formed as a three-dimensional body;

the structure comprising open through pores and dead-ended pores uniformly distributed over inner surfaces of the open pores and connected with the inner surfaces; wherein a cumulative volume of the open pores is greater than a cumulative volume of the dead-ended pores, and wherein an average size of the dead-ended pores ranges-from 0.01 to 1.0 of an average seize of the open pores.

17. The tissue implant according to claim 16, wherein sizes of the open through pores and those of the dead-ended pores are randomly distributed interne from 150 to 300 μm.

18. The tissue implant according to claim 16, wherein a portion of the surface of the three dimensional body is as a barrier layer, the barrier layer being a layer of porous polytetrafluoroethylene with all pores in the layer being closed.

19. The tissue implant according to claim 16, wherein the structure further comprises a reinforcing element.

20. The tissue implant according to claim 19, wherein the reinforcing element is made as a three dimensional structure braided or twisted of a titanium wire.

* * * * *